United States Patent [19]

Butera et al.

[11] Patent Number: 5,104,892

[45] Date of Patent: Apr. 14, 1992

[54] SUBSTITUTED BENZIMIDAZOLE DERIVATIVES POSSESSING CLASS III ANTIARRHYTHMIC ACTIVITY

[75] Inventors: John A. Butera, Kendall Park; Jehan F. Bagli; John W. Ellingboe, both of Princeton, all of N.J.

[73] Assignee: American Home Products Corporation, New York, N.Y.

[21] Appl. No.: 612,727

[22] Filed: Nov. 13, 1990

Related U.S. Application Data

[60] Continuation-in-part of Ser. No. 551,588, Jul. 11, 1990, abandoned, which is a division of Ser. No. 521,787, May 10, 1990, abandoned, which is a continuation-in-part of Ser. No. 451,391, Dec. 11, 1989, abandoned.

[51] Int. Cl.$^5$ ............... C07D 305/12; A61K 31/415; A01N 43/52

[52] U.S. Cl. .................... 514/394; 514/395; 548/329; 548/330

[58] Field of Search .......... 548/329, 330; 514/394, 514/395

[56] References Cited

U.S. PATENT DOCUMENTS

| 4,338,330 | 7/1982 | Gillet et al. | 514/394 |
| 4,647,563 | 3/1987 | Schromm et al. | 514/234 |

*Primary Examiner*—Diana Rivers
*Assistant Examiner*—Matthew V. Grumbling
*Attorney, Agent, or Firm*—Walter Patton

[57] ABSTRACT

This invention relates to N-heteroalkyl-substituted 1-aryloxy-2-propanolamine and proplyamine derivatives possessing anti-arrhythmic activity, to pharmaceutical compositions and to method for production thereof.

7 Claims, No Drawings

SUBSTITUTED BENZIMIDAZOLE DERIVATIVES POSSESSING CLASS III ANTIARRHYTHMIC ACTIVITY

This is a continuation-in-part application of copending application U.S. Ser. No. 07/551,588, filed July 11, 1990, now abandoned, which is in turn a divisional application of copending application U.S. Ser. No. 07/521,787, filed May 10, 1990, now abandoned, which is in turn a continuation-in-part application of copending application U.S. Ser. No. 07/451,391, filed Dec. 11, 1989, now abandoned.

BACKGROUND OF THE INVENTION

Class III antiarrhythmic agents may be categorized as having the ability to markedly prolong dog Purkinje fiber action potential duration without producing significant changes in maximal upstroke velocity. Unlike Class I anti-arrhythmic agents, a pure Class III agent displays no effect on cardiac sodium channels. The electrophysiologic properties of a compound defining a Class III activity profile are observed in vivo as negligible effects on atrial, ventricular and H-V conduction lines while producing a marked increase (greater than 20 percent) in both the atrial and ventricular refractory period. In contrast, Class I agents will demonstrate a marked slowing of ventricular conduction velocity, generally without significant changes in the refractory period. Recent reviews of these agents are by: Bexton et al., Pharmac. Ther., 17, 315-55 (1982); Vaughan-Williams, J. Clin. Pharmacol., 24, 129-47 (1984); and Steinberg et al., Ann. Rep. Med. Chem., 21, 95-108 (1986).

The following workers have reported the selective Class III antiarrhythmic activity of the dextro enantiomer of 4-(2-isopropylamino-1-hydroxyethyl)-methanesulfonamide (MJ-1999, Sotalol): Taggart et al., Clin. Sci., 69, 631-636 (1985) and McComb et al., J. Am. Coll. Cardiol., 5, 438 (1985).

Wohl et al., disclose N-[2-(diethylamino)ethyl]-4-[(methylsulfonyl)amino]-benzamide hydrochloride as a potential class III antiarrhythmic agent in U.S. Pat. No. 4,544,654, Oct. 1, 1985.

Cross et al., have recently reported various N-heterocycle methyl substituted α-phenylethylamine derivatives as useful antiarrhythmic agents in European Patent 0281254, Sept. 7, 1988, as well as other alkyl-sulfonamide compounds reported in European Patent 0286277 and European Patent 0286278, Oct. 12, 1988.

DESCRIPTION OF THE INVENTION

In accordance with this invention, there is provided a group of antiarrhythmic agents classified by their pharmacological profile as Class III antiarrhythmic agents of the formula (I):

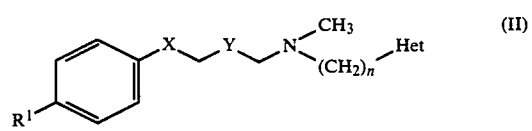
(I)

wherein $R^1$ is alkylsulfonamido of 1 to 6 carbon atoms, arylsulfonamido of 6 to 10 carbon atoms, perfluoroalkylsulfonamido of 1 to 6 carbon atoms, perfluoroalkylamido of 1 to 6 carbon atoms, alkylsulfone or alkylsulfoxide of 1 to 6 carbon atoms, $NO_2$, $CN$, or 1-imidazoyl; $R^2$ is straight or branched alkyl chain of 1 to 6 carbon atoms; X is O, S, or $NR^3$ wherein $R^3$ is H or a straight or branched alkyl chain of 1 to 6 carbon atoms; Y is $CH_2$ or CHOH; n is 0 or 1; Het is selected from the group consisting of

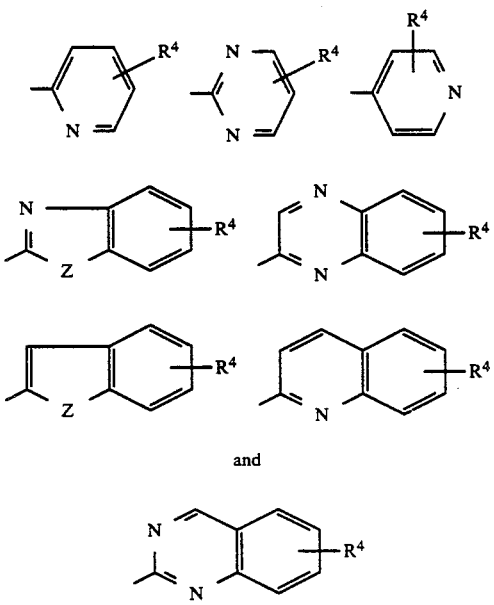

and

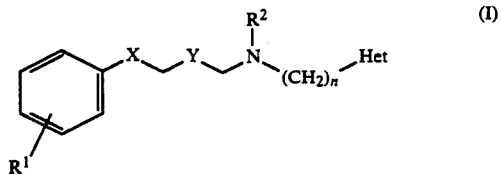

wherein $R^4$ is H, $-NHSO_2$ ($C_1$ to $C_6$ alkyl), $-NHCO$ ($C_1$ to $C_6$ alkyl) or $NO_2$; and Z is O, S, or $NR^5$ wherein $R^5$ is H, $C_1$ to $C_6$ alkyl or the alkylsulfonamido of 1 to 6 carbon atoms and the pharmaceutically acceptable salts thereof.

A preferred aspect of the present invention are the compounds of formula (II)

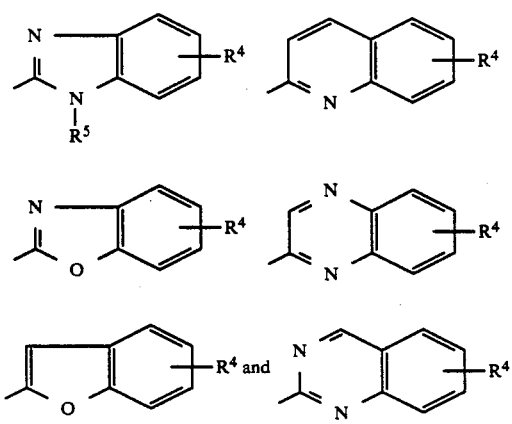
(II)

wherein $R^1$ is $NO_2$ or methylsulfonamido; X is O or S; Y is $CH_2$ or CHOH; n is 0 or 1; and Het is selected from the group consisting of wherein R[4] is H or methylsulfonamido; R[5] is H or $C_1$ to $C_6$ alkyl and the pharmaceutically acceptable salts thereof.

A further preferred aspect of the present invention are the compounds

N-[4-[2-hydroxy-3-[methyl(2-quinolinylmethyl)amino]-propoxy]phenyl]methanesulfonamide;

N-[4-[3-[methyl(2-quinolinylmethyl)amino]propoxy]-phenyl]methanesulfonamide;

N-[4-[3-[methyl(2-quinoxalinylmethyl)amino]propoxy]-phenyl]methanesulfonamide;

1-[(1H-benzimidazol-2-ylmethyl)methylamino]-3-(4-nitrophenoxy)-2-propanol;

N-[4-[3-[(1H-benzimidazol-2-ylmethyl)methylamino]-2-hydroxypropoxy]phenyl]methanesulfonamide;

1-[methyl(2-quinolinylmethyl)amino]-3-(4-nitrophenoxy)-2-propanol;

1-[(2-benzofuranylmethyl)methylamino]-3-(4-nitrophenoxy)-2-propanol;

N-[4-[3-[(2-benzofuranylmethyl)methylamino]-2-hydroxypropoxy]phenyl]methanesulfonamide;

1-[(2-benzoxazolylmethyl)methylamino]-3-(4-nitrophenoxy)-2-propanol;

N-[4-[3-[methyl(1-methyl-1H-benzimidazol-2-yl)amino]propoxy]phenyl]methanesulfonamide;

N-[4-[[3-[methyl(1-methyl-1H-benzimidazol-2-yl)amino]propyl]thio]phenyl]methanesulfonamide;

and the pharmaceutically acceptable salts thereof.

It is to be understood that the definition of the compounds of formula (I) and (II) encompass all possible stereoisomers and mixtures thereof which possess the activity discussed below. In particular, it encompasses racemic modifications and any optical isomers which possess the indicated activity.

The pharmaceutically acceptable salts of the antiarrhythmic agents of this invention are prepared directly by neutralization of the free base. These physiologically acceptable salts may be formed with organic or inorganic acids, such as hydrochloric, hydrobromic, phosphoric, sulfuric, sulfamic, nitric, methylsulfonic, acetic, maleic, succinic, fumaric, tartaric, citric, salicylic, lactic, napthalenesulfonic acid and the like.

The compounds of this invention wherein Y is CHOH may be prepared by reaction of an appropriately substituted aryl epoxide with the required secondary amine in solvents such as acetone or acetonitrile:

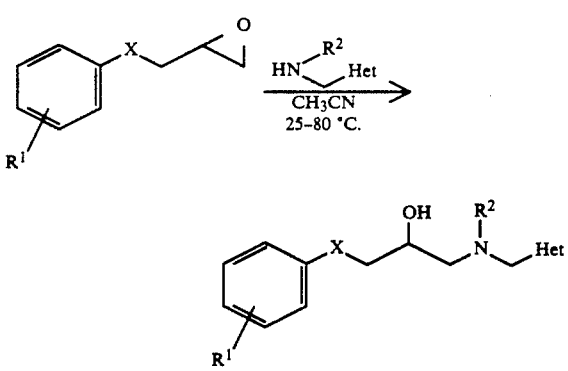

wherein $R^1$, $R^2$, Het and X are as defined above.

When Y is $CH_2$ and n is 1, the compounds can be prepared by the reaction of an appropriately substituted alkyl halide with the required secondary amine in the presence of a suitable base in solvents such as acetone or acetonitrile:

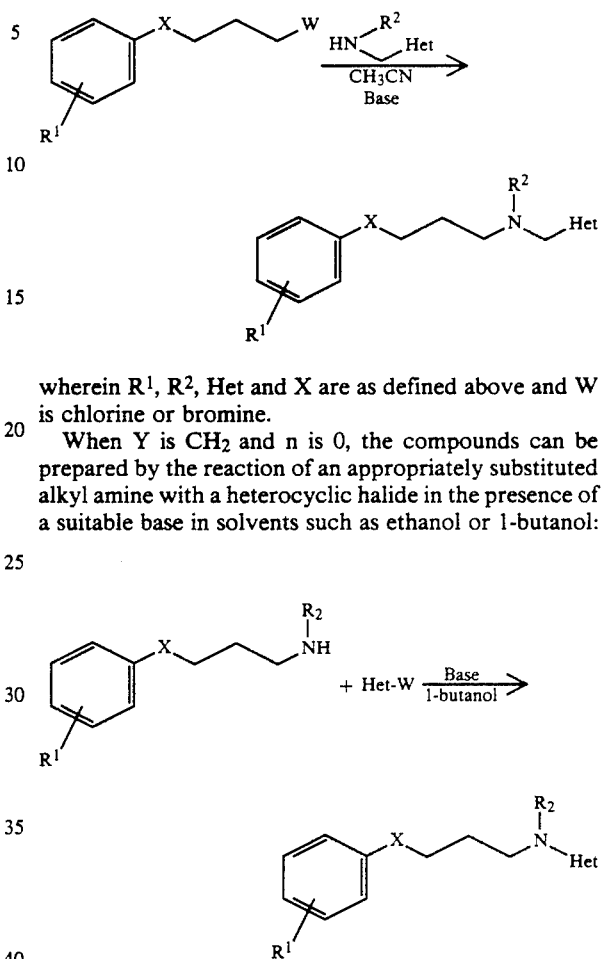

wherein $R^1$, $R^2$, Het and X are as defined above and W is chlorine or bromine.

When Y is $CH_2$ and n is 0, the compounds can be prepared by the reaction of an appropriately substituted alkyl amine with a heterocyclic halide in the presence of a suitable base in solvents such as ethanol or 1-butanol:

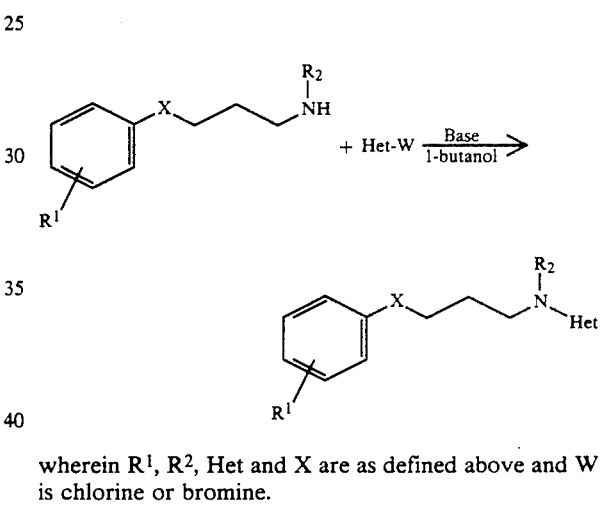

wherein $R^1$, $R^2$, Het and X are as defined above and W is chlorine or bromine.

These reactants are generally known compounds or otherwise are routinely prepared by techniques well within the skill of the chemist.

The compounds of this invention demonstrate antiarrhythmic activity when tested in the standard experimental animal in accordance with the following procedure.

VENTRICULAR FIBRILLATION THRESHOLD

Mongrel dogs of both sexes weighing 12 to 18 kg were anesthetized with sodium pentobarbital (35 mg/kg i.v. supplemented with 5 mg/kg/h) and artificially ventilated with room air (minute volume: 200 mL/kg).

A right thoracotomy was performed at the fifth intercostal space and the heart suspended in a pericardial cradle. Bipolar electrodes for stimulation were sutured to the free wall of the right atrium and to the right ventricle.

Arterial blood pressure and lead II ECG were displayed on a chart recorder and monitored on an oscilloscope. The dog heart was paced by a stimulus for driving a constant current isolation unit.

Ventricular fibrillation threshold (VFT) was determined during atrial pacing at 2.5 Hg. Trains of 4-msec duration square-wave pulses (50 Hz, 200-msec duration)

were delivered to the right ventricle via the epicardial bipolar electrode (silver contacts 1 mm in diameter and 5 mm apart embedded in acrylic matrix). Trains of pulses were delivered every 12th paced beat and were timed to terminate with the end of the T wave of the ECG. Current intensity was increased progressively until ventricular fibrillation (VF) occurred. The lowest current intensity producing VF was defined as the ventricular fibrillation threshold (VFT). When fibrillation occurred the heart was defibrillated within 10 seconds from the onset of fibrillation using a defibrillator charged to 10 J. After defibrillation the animal was allowed to recover for at least 30 minutes or until the ECG returned to normal. VFT was measured twice before drug administration to establish a stable pre-drug threshold.

Dogs were randomized to receive either test drug or vehicle by i.v. route. Animals treated with vehicle do not show any significant increase of VFT. The ability of test agents to elevate the threshold generally is accepted as an indication of potential antifibrillary activity, as vehicle-treated animals on repeated trials do not show any appreciable increase of VFT. This conclusion is supported by the observation that a substantial fraction of the animals treated with the test drug spontaneously defibrillate and return to sinus rhythm. Spontaneously defibrillation of vehicle treated animals is an exceedingly rare phenonmenon.

| Ventricular Fibrillation Threshold in Dog (n = 6; x + S.E.) | |
|---|---|
| Pre-Drug Vehicle | Cmpd 4 (5 mg/kg) |
| 8 + 2* | 25 + 7* |

*Current threshold in mA necessary to induce fibrillation.
*2 to the 6 animals defibrillated spontaneously

CARDIAC ELECTROPHYSIOLOGY

The compounds of this invention display a Class III antiarrhythmic profile. The Class III antiarrhythmic activity was established in vitro and in vivo in accordance with the following standard test procedures:

IN VITRO

Bundles of free-running Purkinje fibers with attached myocardium obtained from either ventricle of adult dog heart were pinned without stretching to the bottom of a 10 mL tissue chamber and continuously superfused with oxygenated Tyrode's solution at a flow rate of 5 mL/minute. The composition of the Tyrode's solution was (mM): NaCl, 138; KCl 4; $CaCl_2$, 2; $MgCl_2$, 0.5; $NaHCO_3$, 24; dextrose, 5.5. The solution was aerated with 95% $O_2$—5% $CO_2$ at 37° C. Bath temperature was maintained at 37°±0.5° C. by circulating the pre-warmed superfusate through a thermostatically controlled water bath immediately prior to entering the tissue chamber.

The preparations were stimulated through bipolar Teflon-coated silver wires, bared at the tips, placed on the endocardial surface of the attached myocardium, using a digital stimulator set to deliver constant current pulses 1.5-msec in duration at cycle lengths of 300 or 1000 msec. Stimulus strength was set at approximately 2× diastolic threshold, and adjusted as required throughout the experiment. All preparations were allowed to equilibrate in the tissue chamber for at least 1 hour before measurements were begun. Subsequently, a minimum of 60 minutes were allowed for equilibration with each drug-containing superfusate before post-drug measurements were made. Impalements were made at 6 to 10 sites throughout the preparation before and after drug exposure. Offset potentials were rechecked after each impalement.

Glass microelectrodes filled with 3M KCl were coupled to high impedance negative capacitance electrometers and Ag/AgCl half-cells used as reference electrodes. The first derivative of the action potential upstroke ($V_{max}$) was obtained using an analog differentiator circuit, coupled to a peak-hold circuit that retained the recorded value of $V_{max}$ for 30 to 70-msec. Action potential and $V_{max}$ tracings were displayed on a storage oscilloscope, and photographed for later analysis. In addition, chart paper recordings of $V_{max}$ were obtained using the peak-hold device output.

Fresh stock solutions of drug were prepared for each experiment. Compounds were dissolved in distilled water at total concentrations of 1 to 10 mg/mL, and subsequently diluted to a final concentration of 3 to 10 $\mu M$ in appropriate volumes of normal Tyrode's solution for evaluation.

Action potential (AP) parameters measured included: diastolic take-off potential (or activation voltage, $V_{(act)}$; AP overshoot ($V_{os}$); AP duration measured as the time taken to repolarize to −20 mV ($APD_{-20}$), −60 mV ($APD_{-60}$), and −80 mV ($APD_{-80}$); and maximal upstroke velocity ($V_{max}$). An increase in $APD_{-60}$ that occurred without a significant change in $V_{max}$ was taken, by definition, to indicate Class III antiarrhythmic activity "in vitro".

IN VIVO

Mongrel dogs of both sexes weighing 12 to 18 kg were anesthetized with sodium pentobarbital (35 mg/kg i.v. supplemented with 5 mg/kg/h) and artificially ventilated with room air (minute volume: 200 mL/kg).

The heart was exposed by a right thoracotomy performed at the fifth intercostal space and suspended in a pericardial cradle. Epicardial electrodes for stimulation and recording were sutured to the free wall of the lower right atrium and near the base of the right ventricle. Each electrode set contained a linear array of electrodes consisting of 1 bipolar stimulating electrode and 2 bipolar recording electrodes embedded in a rigid acrylic matrix. The stimulating bipole was 7 mm from the proximal recording electrode, which in turn was 10 mm from the distal recording bipole. Each electrode array was oriented to be parallel to the epicardial fiber axis.

Arterial blood pressure and lead II ECG were displayed on a chart recorder and monitored on an oscilloscope. Conduction times and refractory periods were measured during pacing at a cycle length of 300 msec. The dog heart was paced by a stimulator driving a constant current isolation unit. Electrical signals from the atrial and ventricular electrodes were displayed on a digital oscilloscope and recorded by a ink-jet recorder. Diastolic threshold was determined before and after each trial.

Refractory periods of the right atrium and right ventricle (AERP and VERP) were determined by introducing an extrastimulus ($S_2$) every 8 paced beats ($S_1$). The extrastimulus was followed by a 4-second rest interval during which no pacing occurred. Both $S_1$ and $S_2$ were of identical intensity (twice threshold) and duration (2 msec). The $S_1$-$S_2$ interval was gradually decreased in 2-msec steps until the extra-stimulus failed to induce a propagated response. This $S_1$-$S_2$ interval was considered to define effective refractory period.

Atrial and ventricular (ACT and VCT) conduction times were measured as the time interval between the 2 electrograms recorded at the proximal and distal sites of the recording electrode array. The time of activation for electrograms with predominantly biphasic complexes was taken as the moment when the trace crossed the zero reference line, and for triphasic complexes, as the peak of the major deflection.

Animals received the test compound by i.v. injection. Drugs were administered cumulatively at the following dose levels: 1, 2.5, 5, 7.5, 10 mg/kg. Each dose was administered over a 3 minute period. Electrophysiologic testing was performed 15 minutes following the end of dosing. Every 30 minutes the dog received the next incremental dose.

Vehicle-treated animals did not show any significant change of the electrophysiologic parameters. An increase in ERP that occurred without a significant decrease of CT was taken, by definition to indicate "in vivo" Class III antiarrhythmic activity.

The results of the assays are set forth in the table below:

| | Biological Data | | | | | | | | | |
|---|---|---|---|---|---|---|---|---|---|---|
| | Purkinje Fiber 3 μM | | | | Anesthetized Dog (5 mg/kg) | | | | | |
| | BCL = 300 | | BCL = 1000 | | BCL = 300 | | | | | |
| Example | APD$_{-60}$ | V$_{max}$ | APD$_{-60}$ | V$_{max}$ | AERP | VERP | ACT | VCT | HR | BP |
| 1 | 71 | 1* | | | 71 | 17 | −4 | −3 | −24 | −22 |
| 2Ψ | 61 | 7 | 38 | 9 | 41 | 18 | 26 | −6 | −20 | −22 |
| 3 | (did not pace) | | 129 | 8 | 90 | 14 | −5 | −8 | −25 | −13 |
| 7 | 18 | 2 | 32 | 15 | | | | | | |
| 6 | 17 | 2 | 43 | 1 | 36 | 11 | −8 | −6 | 8 | −8 |
| 5 | 8 | 12 | 26 | 26 | 25 | 13 | −7 | 0 | −23 | 8 |
| 4 | 27 ± 4 (n = 3) | −9 ± 3 | 62 ± 10 | −7 ± 6 | 51 (n = 2) | 27 | −11 | 0 (n = 2) | −22 | −17 |
| 8 | 22 | +3 (n = 2) | 45 | 5 | 52 (n = 2) | 30 | −6 | 1 | −21 | −8 |
| 9 | 27 | −1 | 43 | −4 | | | | | | |
| 10# | 44 | 1 | 140 | 6 | | | | | | |

*Paced at 500 msec
ΨDosed at 10 mg/kg in anesthetized dog and at 10 μM in Purkinje fiber
1 μM Based upon the activity profile elicted by the compounds of this invention in the above-described standard scientifically recognized test models, the compounds are established as antiarrhythmic agents useful in the treatment of cardiac arrhythmia and conditions characterized by coronary arteries vasospasm. For that purpose, the compounds may be administered orally or parenterally in suitable dosage forms compatible with the route of administration, whether oral, intraperitoneal, intramuscular, intravenous, internasal, buccal, etc. The effective dose range determined in the animal test models has been established at from about 1 to about 5 milligrams per kilogram host body weight (preferably from 2 to 10 mg/kg) i.v., and from about 2 to about 10 mg/kg (preferably 5 to 20 mg/kg) p.o., to be administered in single or plural doses as needed to relieve the arrhythmatic dysfunction. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose (e.g. from about 50 milligrams to about 400 milligrams) of the active ingredient alone or in combination with adjuvants needed for conventional coating, tableting, solubilizing, flavoring or coloring. Parenteral administration with liquid unit dosage forms may be via sterile solutions or suspensions in aqueous or oleaginous medium. Isotonic aqueous vehicle for injection is preferred with or without stabilizers, preservatives and emulsifiers.

The following examples illustrate the preparation of a representative number of compounds of this invention.

EXAMPLE 1

1-[(1H-Benzimidazol-2-ylmethyl)methylamino]-3-(4-nitrophenoxy)-2-propanol Dihydrochloride Step 1) Preparation of 1-p-Nitrophenoxy-2,3-propene To a solution of p-nitro sodiumphenoxide (30 g, 0.186 mol) in DMF (400 mL) was added allyl bromide (24 mL, 0.28 mol). The reaction mixture was stirred under a nitrogen atmosphere at room temperature for 48 hours, then diluted with water (300 mL) and extracted with ether (3×100 mL). The combined organic fraction was diluted with pentane until it became turbid. It was then washed with water (2×100 mL), dried (MgSO$_4$), and concentrated to afford 27.5 g of product (83%) as a red oil of sufficient purity to use in the next step.

$^1$H NMR (CDCl$_3$): δ8.19 (d, 2H, J=8 Hz, ArH̲), 6.97 (d, 2H, J=8 Hz, ArH̲), 6.17 (m, 1H, —CH̲=CH$_2$), 5.40 (m, 2H, —CH=CH̲$_2$), 4.65 (d, 2H̲, J=6 Hz, O—CH$_2$—).

Step 2) Preparation of 1,2-Epoxy-3-(p-nitrophenoxy)propene

To a solution of 1-p-nitrophenoxy-2,3-propene (19.25 g, 0.107 mol) in dry methylene chloride (300 mL) was slowly added meta-chloroperbenzoic acid (24.13 g, 0.14 mol). The reaction mixture was stirred under a nitrogen atmosphere for 48 hours. The mixture was filtered and the filtrate was concentrated to afford a yellow residue. Trituration of the yellow residue with ether yielded the crude product as yellow crystals. Purification by flash chromatography afforded 11.75 g (56%) of product as a light yellow solid m.p. 63°-65° C.

$^1$H NMR (CDCl$_3$): δ8.15 (d, J=8.2 Hz, 2 ArH̲), 6.95 (d, J=8.2 Hz, 2 ArH), 4.36 and 3.98 (2m, —OCH̲$_2$—CH), 3.36 (m, 1H, epoxide methine), 2.92 and 2.76 (2m, 2H, epoxide methylene).

Anal. Calcd.: C, 59.19; H, 5.87; N, 6.27; Found: C, 59.51; H, 5.84; N, 6.31.

Step 3) Preparation of 2-(Methylaminomethyl)benzimidazole

2-Chloromethylbenzimidazole (3.00 g, 18.01 mmol) was dissolved in aqueous methylamine (50 mL, 40 wt % in H$_2$O) at 10° C. under N$_2$. After 30 minutes, the reaction mixture was warmed to room temperature and stirred for 4 hours. Water was added and the mixture extracted with methylene chloride. The organic phase was dried (MgSO$_4$) and concentrated to afford crude product which was purified by HPLC (gradient methanol/methylene chloride) to afford 0.650 g (22%) of pure product as a tan solid.

$^1$H NMR (CDCl$_3$): δ7.56 (m, 2H, ArH), 7.22 (m, 2H, ArH), 4.07 (s, 3H, CH$_2$NHCH$_3$), 2.51 (s, 3H, NHCH$_3$).

Step 4) Preparation of 1-[(1H-Benzimidazol-2-ylmethyl)methylamino]-3-(4-nitrophenoxy-2-propanol Dihydrochloride 2-(Methylaminomethyl)benzimidazole (0.459 g, 3.07 mmol) was added to a solution of 1,2-epoxy-3-(p-nitrophenoxy)propane (0.600 g, 3.07 mmol) in acetonitrile (10 mL). The reaction mixture was stirred at reflux for 18 hours, cooled and concentrated in vacuo. The residue was purified by chromatotron (10% MeOH/CH$_2$Cl$_2$), then treated with ethanolic HCl and ether to afford 0.450 g (34%) of the product as a pale yellow solid dihydrochloride salt m.p. 207°–209° C.

$^1$H NMR (DMSO-d$_6$): δ8.20 (d, J=9.22 Hz, 2H, ArH), 7.73 (m, 2H, ArH), 7.39 (m, 2H, ArH), 7.13 (d, J=9.32 Hz, 2H, ArH), 4.74 (s, 2H, C—CH$_2$—N—CH$_3$), 4.45 (br m, 1H, CHOH), 4.15 (m, 2H, OCH$_2$), 3.43 and 3.37 (m, 2H, —CHOHCH$_2$—N—), 2.95 (s, 3H, NCH$_3$).

IR (KBr, cm$^{-1}$): 3280 (NH⊕), 1500 (C=N).

MS (m/e): 357 (MH$^+$, 94%), 133 (100%).

Anal Calcd: C, 50.35; H, 5.16; N, 13.05; Found: C, 50.09; H, 5.02; N, 13.04.

EXAMPLE 2

N-[4-[3-[(1H-Benzimidazol-2-ylmethyl)methylamino]-2-hydroxypropoxy]phenylmethanesulfonamide

Step 1) Preparation of 3-[(4-Amino)phenoxy]-1-propene

To 3-[(4-nitro)phenoxy]-1-propene, prepared by the process of Example 1, Step 1, (12.65 g, 70.67 mmol) in concentrated HCl (85 mL) at 0° C., was slowly added stannous chloride (48 g, 212 mmol). After stirring for 20 minutes at 55° C., the mixture was cooled to 0° C. and carefully basified with 50% NaOH. The cloudy mixture was extracted with ether. The organic phase was decolorized (charcoal), dried (MgSO$_4$), and concentrated to afford product (8.50 g, 81%) as a yellow oil which was used directly in the next step.

$^1$H NMR (CDCl$_3$): δ7.05 (m, 4H, ArH), 6.4 (m, 1H, OCH$_2$—CH=CH$_2$), 5.70 (m, 2H, CH$_2$CH=CH$_2$), 4.80 (d, 2H, OCH$_2$CH=CH$_2$).

Step 2) Preparation of N-[4-(2-Propenoxy)phenyl]methanesulfonamide

Methanesulfonyl chloride (5.06 mL, 65.32 mmol) was added to a stirred solution of 3-[(4-amino)phenoxy]-1-propene (8.11 g, 54.43 mmol) in pyridine (80 mL) at 0° C. The mixture was stirred for 72 hours and was then poured slowly into ice-water and extracted with ether. The organic phase was washed with cold 1N HCl and was then extracted with 1N NaOH solution. The aqueous phase was acidified and the product (9.05 g, 73%) precipitated out as a white solid.

$^1$H NMR (CDCl$_3$): δ7.18 (d, J=6.75 Hz, 2H ArH), 6.88 (d, J=8.94 Hz, 2H ArH), 6.00 (m, 1H, CH$_2$CH=CH$_2$), 5.40 and 5.30 (2m, OCH=CH$_2$), 4.50 (m, OCH$_2$CH=CH$_2$).

Anal. Calcd.: C, 52.85; H, 5.76; N, 6.16; Found: C, 52.80; H, 5.63; N, 5.99.

Step 3) Preparation of 1-[(4-Methanesulfonamido)phenoxy]-2,3-propeneoxide m-Chloroperoxybenzoic acid (12.16 g, 70.48 mmol) was added to a solution of N-[4-(2-propeneoxy)phenyl]methanesulfonamide (8.00 g, 35.24 mmol) in methylene chloride (120 mL). The mixture was stirred overnight at reflux, cooled, and filtered. Concentration afforded crude product which was purified by flash chromatography using 1:1 hexane/ethyl acetate. Yield 5.55 g (65%) of white solid.

$^1$H NMR (CDCl$_3$): δ7.17 (d, J=6.87 Hz, 2H ArH), 6.90 (d, J=8.93 Hz, 2H, ArH), 6.40 (br s, NHSO$_2$CH$_3$), 4.20 (dd, J$_1$=5.54 Hz, J$_2$=2.98 Hz, 1H, epoxide CH$_2$), 3.90 (dd, H$_1$=5.54, J$_2$=5.78 Hz, 1H, epoxide CH$_2$), 3.35 (m, 1H, epoxide CH), 2.94 (s, 3H, NHSO$_2$CH$_3$), 2.90 and 2.76 (2m, OCH$_2$).

IR (KBr): 3240 (NH).

MS (m/z): 243 (60% M$^+$), 164 (100%).

Anal. Calcd.: C, 49.37; H, 5.39; N, 5.76; Found: C, 49.69; H, 5.63; N, 5.63.

Step 4) N-[4-[3-[(1H-Benzimidazol-2-ylmethyl)methylamino]-2-hydroxypropoxy]phenylmethanesulfonamide 2-(Methylaminomethyl)benzimidazole, prepared by the procedure of Example 1, Step 3, (0.993 g, 6.16 mmol) was added to a solution of 1,2-epoxy-3-(p-methanesulfonamidophenoxy)propane (1.5 g, 6.16 mmol) in acetonitrile (12 mL). The reaction mixture was stirred at reflux for 18 hours, cooled to 0° C. and vacuum filtered. The solids were washed with cold ether and dried under heated vacuum to afford 1.32 g (53%) of analytically pure product m.p. 163°–165° C.

$^1$H NMR (DMSO-d$_6$): δ9.33 (br s, 1H, NHSO$_2$CH$_3$), 7.52 and 7.44 (m, 2H, ArH), 7.10 (d, J=9.02 Hz, 2H, ArH), 7.09 (m, 2H, ArH), 6.98 (d, J=8.96 Hz, 2H, ArH), 4.93 (br s, 1H, OH), 3.95 (m, 2H, OCH$_2$), 3.79 (s and m, 3H, CH$_3$NCH$_2$ and CHOH), 2.86 (s, 3H, NHSO$_2$CH$_3$), 2.59 and 2.51 (m, 2H, CHOHCH$_2$NCH$_3$), 2.27 (s, 3H, NCH$_3$).

IR (KBr, cm$^{-1}$): 3290 (NH).

MS (m/e): 405 (MH$^+$, 18%), 131 (100%).

Anal Calcd: C, 56.42; H, 5.98; N, 13.85; Found: C, 56.24; H, 5.94; N, 13.81.

EXAMPLE 3

1-[Methyl(2-quinolinylmethyl)amino]-3-(4-nitrophenoxy)-2-propanol Dihydrochloride

Step 1) Preparation of 2-(Methylaminomethyl)quinoline

2-Chloromethylquinoline hydrochloride (3.00 g, 14.01 mmol) was suspended in aqueous methylamine (40 mL, 40 wt % in H$_2$O) at 10° C. under a N$_2$ atmosphere. After 20 minutes, the reaction mixture was warmed to room temperature and stirred for 3 hours. The mixture was diluted with water and extracted with methylene chloride. The organic extracts were dried (MgSO$_4$) and concentrated to afford 2.22 g (92%) of pure product as a brown oil.

$^1$H NMR (CDCl$_3$): δ8.08 (m, 2H, ArH), 7.78 (d, J=8.11 Hz, 1H, quinoline H$_4$), 7.69 (m, 1H, ArH), 7.52

(d, J=7.03 Hz, 1H, ArH), 7.44 (d, J=8.72 Hz, 1H, quinoline H$_3$), 4.06 (s, 2H, CH$_2$NHCH$_3$), 2.55 (s, 3H, NHCH$_3$).

Step 2) Preparation of 1-[Methyl(2-quinolinylmethyl)amino]-3-(4-nitrophenoxy)-2-propanol Dihydrochloride 2-(Methylaminomethyl)quinoline (1.76 g, 10.22 mmol) was added to a solution of 1,2-epoxy-3-(p-nitrophenoxy)propane, prepared by the procedure of Example 1, Step 2, (1.00 g, 5.12 mmol) in acetonitrile (10 mL). The reaction mixture was stirred at reflux for 18 hours, cooled and concentrated in vacuo. The residue was purified by flash column chromatography (3% MeOH—CH$_2$Cl$_2$) and then treated with ethanolic HCl and ether to afford 0.510 g (13%) of product as the white solid dihydrochloride salt m.p. 154°–157° C.

$^1$H NMR (DMSO-d$_6$): δ10.27 (br s, 1H, NH⊕), 8.50 (d, J=8.43 Hz, 1H, quinoline H), 8.17 (d, J=9.28 Hz, 2H, ArH), 8.03 (tr, J=6.89 Hz, 2H, ArH), 7.82 (m, 1H, ArH), 7.72 (d, J=8.46 Hz, 1H, quinoline H), 7.67 (m, 1H, ArH), 7.07 (d, J=9.26 Hz, 2H, ArH), 4.78 (s, 2H, C—CH$_2$NCH$_3$), 4.50 (br m, 1H, CHOH), 4.12 (d, J=5.04 Hz, 2H, OCH$_2$), 3.50 and 3.36 (m, 2H, CHOH—CH$_2$—N), 3.01 (s, 3H, NCH$_3$).

IR (KBr, cm$^{-1}$): 3260 (NH+).

MS (m/e): 368 (MH+).

Anal. Calcd: C, 54.56; H, 5.27; N, 9.54; Found: C, 55.00; H, 5.58; N, 9.16.

EXAMPLE 4

N-[4-[3-[(2-Quinolinylmethyl)methylamino]-2-hydroxypropoxy]phenyl]methanesulfonamide 2-(Methylaminomethyl)quinoline prepared by the procedure of Example 3, Step 1, (1.69 g, 9.86 mmol) in acetonitrile (4 mL) was added to a stirring solution of 1,2-epoxy-3-(p-methanesulfonamidophenoxy)propane, prepared by the procedure of Example 2, Step 3, (2.00 g, 8.22 mmol) in acetonitrile (12 mL). The reaction mixture was heated at reflux for 18 hours, cooled and concentrated in vacuo. The residue was purified by flash column chromatography (10% MeOH—CH$_2$Cl$_2$) and then triturated with ethyl acetate/ether, filtered and dried under heated vacuum to afford 1.52 g (44%) of analytically pure product m.p. 118°–120° C. as a tan solid.

$^1$H NMR (DMSO-d$_6$): δ9.34 (s, 1H, NHSO$_2$CH$_3$), 8.24 (d, J=8.48 Hz, 1H, quinoline H), 7.94 (m, 2H, ArH), 7.72 (m, 1H, ArH), 7.61 (d, J=8.52 Hz, 1H, quinoline H), 7.56 (m, 1H, ArH), 7.11 (d, J=9.01 Hz, 2H, ArH), 6.84 (d, J=8.93 Hz, 2H, ArH), 5.00 (br d, 1H, OH), 3.96 (m, 2H, OCH$_2$), 3.82 (m, 3H, CCH$_2$NCH$_3$+CHOH), 2.87 (s, 3H, NHSO$_2$CH$_3$), 2.61 and 2.49 (CHOHCH$_2$NCH$_3$), 2.28 (s, 3H, NCH$_3$).

IR (KBr, cm$^{-1}$): 3450 (OH), 3180 (NH).

MS (m/e): 416 (MH+, 60%).

Anal Calcd: C, 60.70; H, 6.06; N, 10.11; Found: C, 60.60; H, 6.08; N, 9.85.

EXAMPLE 5

1-[(2-Benzoxazolylmethyl)methylamino]-3-(4-nitrophenoxy)-2-propanol Hydrochloride

Step 1) Preparation of 2-(Chloromethyl)benzoxazole

A mixture of o-aminophenol (4.00 g, 36.6 mmol) and ethyl chloroacetimidate hydrochloride (8.68 g, 54.98 mmol) in ethanol (55 mL) was heated at reflux for 18 hours. The reaction mixture was cooled to room temperature and vacuum filtered. The filtrate was concentrated in vacuo, diluted with methylene chloride and filtered again. The methylene chloride filtrate was dried (MgSO$_4$) and concentrated to afford 3.99 g (65%) of product as a brown oil which was used directly in the next step.

$^1$H NMR (CDCl$_3$): δ7.73 (m, 1H, ArH), 7.56 (m, 1H, ArH), 7.38 (m, 2H, ArH), 4.76 (s, 2H, CH$_2$Cl).

Step 2) Preparation of 2-(Methylaminomethyl)benzoxazole 2-(Chloromethyl)benzoxazole (3.99 g, 23.8 mmol) was dissolved in aqueous methylamine (40 mL, 40 wt % in H$_2$O) at 10° C. under a nitrogen atmosphere. After 20 minutes, the reaction mixture was warmed to room temperature and stirred for 1 hour. The mixture was diluted with water and extracted with methylene chloride. The organic phase was dried (MgSO$_4$) and concentrated to afford crude product which was purified by flash column chromatography (5% MeOH/CH$_2$Cl$_2$) to afford 3.18 g (82%) of pure product as a yellow oil.

$^1$H NMR (CDCl$_3$): δ7.72 (m, 1H, ArH), 7.54 (m, 1H, ArH), 7.33 (m, 2H, ArH), 4.08 (s, 2H, CH$_2$NHCH$_3$), 2.56 (CH$_2$NHCH$_3$).

Step 3) Preparation of 1-[(2-Benzoxazolylmethyl)methylamino]-3-(4-nitrophenoxy)-2-propanol Hydrochloride 2-(Methylaminomethyl)benzoxazole (1.86 g, 11.53 mmol) was added to a solution of 1,2-epoxy-3-(p-nitrophenoxy)propane, prepared by the process of Example 1, Step 2, (1.5 g, 7.68 mmol) in acetonitrile (25 mL). The reaction mixture was heated at reflux for 24 hours and then stirred at room temperature for an additional 24 hours. The mixture was concentrated in vacuo. The residue was purified by chromatotron (10% MeOH—CH$_2$Cl$_2$) then treated with ethanolic HCl and ether to afford 2.12 g (70%) of pure product as the off-white solid hydrochloride salt m.p. 214°–216° C.

$^1$H NMR (DMSO-d$_6$): δ8.20 (d, J=9.13 Hz, 2H ArH), 7.84 (dd, J$_1$=7.67 Hz, J$_2$=0.415 Hz, 1H, ArH), 7.80 (dd, J$_1$=8.50 Hz, J$_2$=1.25 Hz, 1H, ArH), 7.50 (m, 1H, ArH), 7.45 (m, 1H, ArH), 7.14 (d, J=9.33 Hz, 2H, ArH), 4.87 (s, 2H, C—CH$_2$NCH$_3$), 4.50 (br m, 1H, CHOH), 4.15 (d, J=4.77 Hz, 2H, OCH$_2$), 3.54 (m, 2H, CHOH—CH$_2$N), 3.05 (s, 3H, NCH$_3$).

IR (KBr, cm$^{-1}$): 3160 (OH+NH⊕).

MS (m/e): 358 (MH+).

Anal Calcd: C, 54.90; H, 5.12; N, 10.67; Found: C, 55.35; H, 5.11; N, 10.68.

EXAMPLE 6

N-[4-[3-[(2-Benzofuranylmethyl)methylamino]-2-hydroxypropoxy]phenyl]methanesulfonamide

Step 1) Preparation of Benzofuran-2-methanol

1 Molar diborane in tetrahydrofuran (61.6 mL, 61.6 mmol) was added dropwise over 10 minutes to a stirred solution of benzofuran-2-carboxylic acid (5.00 g, 30.8 mmol) in tetrahydrofuran (50 mL) at 0° C. Stirring was continued at 0° C. for 30 minutes, then at room temperature for 18 hours. The reaction mixture was quenched carefully by slow addition of 1:1 THF/H$_2$O, and extracted with ether. The organic extracts were dried (MgSO$_4$) and concentrated to afford 3.58 g (78%) of product as a colorless oil.

$^1$H NMR (DMSO-d$_6$): δ7.57 (m, 2H, ArH), 7.27 (m, 2H, ArH), 6.75 (s, 1H, CH=C—), 4.58 (s, 2H, CH$_2$OH).

Step 2) Preparation of 2-(Chloromethyl)benzofuran

Thionyl chloride (5.14 mL, 70.46 mmol) was added dropwise to a solution of benzofuran-2-methanol (3.58 g, 23.48 mmol) and pyridine (10 drops) in methylene chloride (60 mL). Stirring was continued at room temperature for 18 hours. The mixture was carefully diluted with water and extracted with methylene chloride. The organic extracts were washed with aqueous sodium bicarbonate, dried (MgSO$_4$) and concentrated to afford crude product which was purified by flash column chromatography (10% EtOAc/hexanes) to afford 2.77 g (69%) of pure product as a yellow oil.

$^1$H NMR (CDCl$_3$): δ7.52 (m, 2H, ArH), 7.27 (m, 2H, ArH), 6.73 (s, 1H, CH=C—), 4.69 (s, 2H, CH$_2$Cl).

Step 3) Preparation of 2-(Methylaminomethyl)benzofuran 2-(Chloromethyl) benzofuran (2.77 g, 16.63 mmol) was dissolved in aqueous methylamine (40 mL, 40 wt % in H$_2$O) at 10° C. under a nitrogen atmosphere. After 10 minutes, the reaction mixture was warmed to room temperature and stirring was continued for 72 hours. The mixture was diluted with water and extracted with methylene chloride. The organic phase was dried (MgSO$_4$) and concentrated to afford crude product which was purified by flash column chromatography (10% MeOH/CH$_2$Cl$_2$) to afford 1.00 g (37%) of pure product as a pale yellow oil.

$^1$H NMR (CDCl$_3$): δ7.48 (m, 2H, ArH), 7.21 (m, 2H, ArH), 6.56 (s, 1H, CH=C—), 3.89 (s, 2H, CH$_2$NHCH$_3$), 2.47 (s, 3H, NHCH$_3$).

Step 4) Preparation of N-[4-[3-[(2-Benzofuranylmethyl)methylamino]-2-hydroxypropoxy]phenyl]methanesulfonamide 2-(Methylaminomethyl)benzofuran (0.927 g, 6.16 mmol) was added to a solution of 1,2-epoxy-3-(p-methanesulfonamidophenoxy)propane (1.4 g, 6.16 mmol) in acetonitrile (12 mL). The reaction mixture was heated at reflux for 48 hours, cooled and concentrated in vacuo. The residue was purified by chromatotron (10% MeOH/CH$_2$Cl$_2$) twice to afford an oil which was treated with ethanolic HCl and ether to give 0.640 g (25%) of pure product as the white solid hydrochloride salt m.p. 182°-183° C.

$^1$H NMR (DMSO-d$_6$): δ9.14 (s, 1H, NHSO$_2$CH$_3$), 7.72 (d, J=7.68 Hz, 1H, ArH), 7.61 (d, J=6.39 Hz, 1H, ArH), 7.30 (tr, J=7.34 Hz, 7.25 Hz, ArH), 7.23 (s, 1H, CH=C—), 7.13 (d, J=8.85 Hz, 2H, ArH), 6.88 (d, J=8.93 Hz, 2H, ArH), 6.02 (br m, 1H, OH), 4.65 (br s, 2H, —C—CH$_2$NCH$_3$), 4.41 and 4.29 (br m, 1H, CHOH), 3.91 (d, J=4.98 Hz, 2H, OCH$_2$), 3.34 (s, 3H, NHSO$_2$CH$_3$), 3.26 (m, 2H, CHOH—CH$_2$N), 2.87 (s, 3H, NCH$_3$).

IR (KBr, cm$^{-1}$): 3320 (NH).
MS (m/e): 404 (M+), 131 (100%).
Anal Calcd: C, 54.48; H, 5.71; N, 6.35; Found: C, 54.43; H, 5.64; N, 6.15.

EXAMPLE 7

1-[(2-Benzofuranylmethyl)methylamino]-3-(4-nitrophenoxy)-2-propanol Hydrochloride 2-(Methylaminomethyl)benzofuran, prepared by the process of Example 6, Step 3, (0.991 g, 6.14 mmol) was added to a solution of 1,2-epoxy-3-(p-nitrophenoxy)propane, prepared by the process of Example 1, Step 2, (0.600 g, 3.07 mmol) in acetonitrile (10 mL). The reaction mixture was stirred at reflux for 18 hours, cooled and concentrated in vacuo. The residue was purified by flash column chromatography (5% MeOH/CH$_2$Cl$_2$), then treated with ethanolic HCl and ether to afford 0.8 g (66%) of pure hydrochloride salt as a pale yellow solid m.p. 208°-209° C.

$^1$H NMR (DMSO-d$_6$): δ10.44 (br s, 1H, NH⊕), 8.20 (d, J=9.28 Hz, 2H, ArH), 7.72 (d, J=7.63 Hz, 1H ArH), 7.61 (d, J=8.28 Hz, 1H, ArH), 7.39 (m, 1H, ArH), 7.30 (m, 1H, ArH), 7.25 (s, 1H, CH=C—), 7.12 (d, J=9.24 Hz, 2H, ArH), 6.12 (br s, 1H, OH), 4.65 (s, 2H, C—CH$_2$NCH$_3$), 4.49 and 4.37 (br m, 1H, CHOH), 4.13 (d, J=3.86 Hz, 2H, OCH$_2$), 3.39 and 3.29 (m, 2H, CHOH—CH$_2$—N—), 2.87 (s, 3H, NCH$_3$).

IR (KBr, cm$^{-1}$): 3220 (NH⊕).
MS (m/e): 356 (M+), 131 (100%).
Anal Calcd: C, 58.09; H, 5.39; N, 7.13; Found: C, 58.00; H, 5.61; N, 6.92.

EXAMPLE 8

N-[4-[3-[Methyl(2-quinolinylmethyl)amino]propoxy]phenyl]methanesulfonamide

Step 1) Preparation of N-[(4-Nitrophenoxy)propoxy[methyl]]aminomethylquinoline To a stirred suspension of 2-(methylaminomethyl)-quinoline, prepared by the procedure of Example 3, Step 1, (3.67 g, 21.35 mmol), sodium iodide (2.78 g, 18.56 mmol), and potassium carbonate (3.08 g, 138.21 mmol) in acetonitrile (80 mL) was added 3-chloropropyl-4-nitrophenyl ether (4.00 g, 18.56 mmol). The mixture was stirred at 80° C. overnight, concentrated and partitioned between 10% K$_2$CO$_3$ and ethyl acetate. The organic phase was washed with brine, dried (MgSO$_4$), and concentrated to afford an oil. The product was purified by HPLC (10% MeOH/CH$_2$Cl$_2$) to afford 2.34 g (36%) of pure product as a yellow oil.

$^1$H NMR (CDCl$_3$): δ8.2-7.9 (m, 4H, quinoline H), 7.7 (m, 2H, quinoline H), 7.5 (d, J=6 Hz, 2H, ArH), 6.8 (d, J=6.2 Hz, 2H, ArH), 4.1 (t, J=4.8 Hz, 2H, —OCH$_2$), 3.8 (s, 2H, —NCH$_2$), 2.62 (t, J=4 Hz, —CH$_2$N—), 2.35 (s, 3H, NCH$_3$), 2.0 (m, 2H, —CH$_2$CH$_2$CH$_2$—).

Step 2) Preparation of N-[(4-Aminophenoxy)propoxy[methyl]]aminomethylquinoline A mixture of N-[(4-nitrophenoxy)propoxy[methyl]-]aminomethylquinoline (1.97 g, 5.61 mmol) and 5% Pd/C (0.197 g) in ethyl acetate (40 mL) in a Parr reactor was charged with 50 PSI H$_2$ and left overnight. The mixture was then filtered through solka floc and concentrated to afford 1.86 g (100%) of amine as a yellow oil which was used directly in the next step.

$^1$H NMR (CDCl$_3$): δ8.1 (m, 2H, quinoline H), 7.8-7.4 (m, 4H, quinoline H), 6.70 (br q, 4H, ArH), 3.95 (t, J=4.8 Hz, —OCH$_2$—), 3.84 (s, 2H, N—CH$_2$—), 3.38 (br s, 2H, —NH$_2$), 2.64 (t, J=4.8 Hz, —CH$_2$—N—), 2.31 (s, 3H, —NCH$_3$), 1.97 (m, 2H, —CH$_2$—CH$_2$—CH$_2$—).

Step 3) Preparation of N-[4-[3-[(Methyl(2-quinolinylmethyl)amino]propoxy]phenyl]methanesulfonamide Methanesulfonylchloride (0.52 mL, 6.73 mmol) was added dropwise to a stirred solution of N-[(4-aminophenoxy)propoxy[methyl]]aminomethylquinoline (1.80 g, 5.61 mmol) in pyridine (20 mL) at 0° C. The resulting mixture was stirred at room temperature overnight. The reaction was quenched with ice chips and extracted with ethyl acetate. The organic phase was dried (MgSO$_4$), decolorized (charcoal), and concentrated to afford crude product which was purified by chromatotron (5% CH$_3$OH/CH$_2$Cl$_2$) to yield 0.88 g of an oil which was triturated with ether/hexane to form a white solid m.p. 83°–86° C.

$^1$H NMR (CDCl$_3$): δ8.06 (m, 2H, quinoline H), 7.8 (d, J=8.1 Hz, 1H, quinoline H), 7.7 (m, 1H, quinoline H), 7.58 (d, J=8.47 Hz, 1H, quinoline H), 7.52 (m, 1H, quinoline H), 7.15 (d, J=8.85 Hz, 2H, ArH), 6.81 (d, J=8.88 Hz, 2H, ArH), 4.02 (t, J=6.26 Hz, 2H, —OCH$_2$), 3.86 (s, 2H, NCH$_2$—), 2.95 (s, 3H —SO$_2$CH$_3$), 2.66 (t, J=6.93 Hz, —CH$_2$N—), 2.34 (s, 3H, NCH$_3$), 2.01 (m, 2H, —CH$_2$CH$_2$CH$_2$—).

IR (KBr, cm$^{-1}$): 2900 (NH).

MS (m/e): 400 (MH+, 100%), 259, 144.

Anal. Calcd: C, 63.13; H, 6.31; N, 10.52; Found: C, 62.86; H, 6.23; N, 10.30.

EXAMPLE 9

N-[4-[3-[Methyl(2-quinoxalinylmethyl)amino]propoxy]phenyl]methanesulfonamide

Step 1) Preparation of 2-(Bromomethyl)quinoxaline

To a stirring solution of 2-methylquinoxaline (20.0 g, 155 mmol) and benzoyl peroxide (3 g, 12 mmol) in carbon tetrachloride (800 mL) was added 1,3-dibromo-5,5-dimethyl hydantoin (22 g, 77 mmol). The resulting mixture was irradiated with a spotlight (200 watt) for 1.5 hours. The mixture was cooled, filtered, and concentrated to afford crude product which was purified by HPLC (4:1 hexane/EtOAc) to yield 14.0 g (40%) of monobromomethyl product as a grey solid: $^1$H NMR (CDCl$_3$): δ9.00 (s, 1H, ArH), 8.10 (m, 2H, ArH), 7.80 (m, 2H, ArH), 4.72 (s, 2H, BrCH$_2$—Ar); and 15.0 g (35%) of dibromomethyl product as a white solid: $^1$H NMR (CDCl$_3$): δ9.39 (s, 1H, ArH), 8.15 (m, 2H, ArH), 7.90 (m, 2H, ArH), 6.76 (s, 1H, Br$_2$CH—Ar).

Step 2) Preparation of 2-(Methylaminomethyl)quinoxaline

The 2-(bromomethyl)quinoxaline (3.0 g, 13.4 mmol) was added portionwise to a stirring solution of methylamine (30%) in ethanol (100 mL) at 0° C. The reaction was stirred at 0° C. for 2 hours, concentrated, and partitioned between 10% aqueous potassium carbonate/ethyl acetate. The organic phase was dried (MgSO$_4$), decolorized (charcoal) and concentrated. Purification was accomplished by eluting the sample through a short silica plug to yield 1.80 g (78%) of a brown oil.

$^1$H NMR (CDCl$_3$): δ8.85 (s, 1H, ArH), 8.10 (m, 2H, ArH), 7.73 (m, 2H, ArH), 4.15 (s, 2H, NCH$_2$Ar), 2.60 (s, 3H, NCH$_3$).

Step 3) Preparation of 3-Iodopropyl-4-nitrophenyl Ether

To a stirring solution of 4-nitrophenol (10.0 g, 71.94 mmol) in tetrahydrofuran (100 mL) at 0° C. was added triphenylphosphine (22.6 g, 86.33 mmol), 3-iodopropanol (16.73 g, 89.93 mmol), and diethylazodicarboxylate (14.3 mL, 86.33 mmol). The resulting mixture was stirred at 25° C. overnight. The mixture was partitioned between brine and ethyl acetate. The organic phase was dried and concentrated. The residue was triturated with 8:1 ether/ethyl acetate to induce the precipitation of 22 g of triphenylphosphine oxide which was separated by filtration. The filtrate was preabsorbed onto silica gel and flash-chromatographed (5:1 hexane/EtOAc) to afford 17.5 g (79%) of white solid product.

$^1$H NMR (CDCl$_3$): δ8.22 (d, J=8.2 Hz, 2H, ArH), 6.96 (d, J=9.0 Hz, 2H, ArH), 4.15 (t, J=5.8 Hz, 2H, OCH$_2$), 3.37 (t, J=7.0 Hz, 2H, CH$_2$I), 2.31 (m, 2H, CH$_2$CH$_2$CH$_2$I).

Step 4) Preparation of N-[(4-Nitrophenoxy)propoxy[methyl]]aminomethylquinoxaline To a stirred suspension of 2-(methylaminomethyl)-quinoxaline (1.10 g, 6.35 mmol) and potassium carbonate (0.88 g, 6.35 mmol) in 2:1 acetonitrile/ethanol (40 mL) was added 3-iodopropyl-4-nitrophenyl ether (1.95 g, 6.35 mmol). The resulting mixture was heated at 85° C. overnight, concentrated, and partitioned between ethyl acetate and 10% aqueous potassium carbonate. The organic phase was dried (MgSO$_4$), decolorized (charcoal), and concentrated to afford 1.86 g (83%) of product as a yellow semi-solid which was of sufficient purity to use in the next step.

$^1$H NMR (CDCl$_3$): δ8.95 (s, 1H, ArH), 8.10 (d, J=9.4 Hz, 2H, ArH), 8.0 (m, 2H, ArH), 7.72 (m, 2H, ArH), 6.76 (d, J=9.8 Hz, 2H, ArH), 4.09 (t, J=5.4 Hz, 2H, OCH$_2$), 2.67 (t, J=5.2 Hz, 2H, CH$_2$N), 2.41 (s, 3H, CH$_3$N), 2.05 (m, 2H, CH$_2$CH$_2$CH$_2$).

Step 5) Preparation of N-[4-Aminophenoxy)propoxy[methyl]]aminomethylquinoxaline

A mixture of N-[(4-nitrophenoxy)propoxy[methyl]-]aminomethylquinoxaline (1.75 g, 4.97 mmol) and PtO$_2$ (0.14 g, 0.62 mmol) in ethanol (170 mL) was charged with 1 atmosphere H$_2$(g). After 30 minutes, the mixture was filtered through solka floc and concentrated to afford crude product which was purified by HPLC to yield 1.18 g (74%) of a yellow oil.

$^1$H NMR (CDCl$_3$): δ9.00 (s, 1H, ArH), 8.07 (m, 2H, ArH), 7.73 (m, 2H, ArH), 6.70 (d, J=8.2 Hz, 2H, ArH), 6.02 (d, J=9.0 Hz, 2H, ArH), 3.95 (t, J=6 Hz, 2H, OCH$_2$), 3.89 (s, 2H, NCH$_2$Ar), 3.40 (brs, 2H, NH$_2$), 2.68 (t, J=6.6 Hz, 2H, CH$_2$N). 2.33 (s, 3H, NCH$_3$), 1.99 (m, 2H, CH$_2$CH$_2$CH$_2$N).

Step 6) Preparation of N-[4-[3-[Methyl(2-quinoxalinylmethyl)amino]propoxy]phenyl]methanesulfonamide To a stirred solution of N-[(4-aminophenoxy)propoxy[methyl]]aminomethylquinoxaline (0.93 g, 2.89 mmol) and pyridine (0.47 mL, 5.78 mmol) in dichloromethane (20 mL) at 0° C. under N$_2$ was added dropwise methanesulfonyl chloride (0.25 mL, 3.21 mmol). The mixture was warmed to 25° C., stirred for 2.5 hours, and then partitioned between 10% aqueous NaHCO$_3$ and ethyl acetate. The organic phase was washed with brine, dried (MgSO$_4$), decolorized (charcoal), and concentrated to afford 0.93 g (80%) of product as a yellow oil (one spot by TLC). The compound was treated with ethanolic HCl/ether to afford 0.75 g of the hydrochloride salt as a grey powder m.p. 165°–170° C. (dec.).

$^1$H NMR (DMSO-D$_6$): δ9.42 (s, 1H, NHSO$_2$CH$_3$), 9.20 (s, 1H, ArH), 8.16 (m, 2H, ArH), 7.95 (m, 2H, ArH), 7.14 (d, J=9.1 Hz, 2H, ArH), 6.87 (d, J=9.0 Hz, 2H, ArH), 4.84 (m, 2H, NCH$_2$—Ar), 4.05 (t, J=6 Hz,

2H, OCH$_2$—), 3.40 (m, 2H, —CH$_2$CH$_2$CH$_2$N), 2.93 (s, 3H, NCH$_3$), 2.87 (s, 3H, NHSO$_2$CH$_3$), 2.26 (m, 2H, CH$_2$CH$_2$CH$_2$—N).

IR (KBr): 2900 (NH).

MS (m/e): 400 (M+, 5%), 257, 144.

Anal. Calcd: C, 54.98; H, 5.77; N, 12.82; Found: C, 54.76; H, 5.87; N, 12.60.

EXAMPLE 10

N-[4-[3-[Methyl(1-methyl-1H-benzimidazol-2-yl)amino]propoxy]phenyl]methanesulfonamide Hydrochloride

Step 1) Preparation of 1-Chloro-3-(4-nitrophenoxy)propane

To a cooled (5°–10° C.) suspension of KOtBu (1.34 g, 11.96 mmol) in DMSO (5 mL) was added a solution of 4-fluoronitrobenzene (1.61 g, 11.39 mmol) and 3-chloro-1-propanol (1.13 g, 11.96 mmol) in DMSO (5 mL). The cooling bath was removed and stirring was continued for 3 hours. The mixture was diluted with water (100 mL) and extracted with ether. The combined extracts were washed with brine, dried (MgSO$_4$), and concentrated to give a brown oil. Purification by flash chromatography (10% EtOAc/hexane) gave 850 mg (35%) of product as a yellow oil.

$^1$H NMR (DMSO-d$_6$): δ8.21 (dd, J=7.2, 2.3 Hz, 2H), 7.17 (dd, J=7.2, 2.3 Hz, 2H), 4.24 (t, J=6.2 Hz, 2H), 3.80 (t, J=6.4 Hz, 2H), 2.21 (m, 2H).

Step 2) Preparation of 1-Chloro-3-(4-aminophenoxy)propane

A mixture of 1-chloro-3-(4-nitrophenoxy)propane (830 mg, 3.85 mmol), stannous chloride dihydrate (4.3 g, 19.25 mmol), and EtOH (20 mL) was heated under reflux for 3 hours. The mixture was cooled, 2.5N NaOH (19 mL) was added, and the precipitate was removed by filtration. The filtrate was concentrated to 10 mL and extracted with EtOAc. The extracts were dried (MgSO$_4$) and concentrated to give 700 mg (98%) of product as a brown oil.

$^1$H NMR (DMSO-d$_6$): δ6.66 (dd, J=6.6, 2.3 Hz, 2H), 6.51 (dd, J=6.6, 2.3 Hz, 2H), 4.67 (br s, 2H), 3.93 (t, J=6.6 Hz, 2H), 3.76 (t, J=6.6 Hz, 2H), 2.09 (m, 2H).

Step 3) Preparation of N-[4-(3-Chloro-1-propyloxy)phenyl]methanesulfonamide To a cooled (0° C.), stirred solution of 1-chloro-3-(4-aminophenoxy)propane (680 mg, 3.66 mmol) and pyridine (319 mg, 4.03 mmol) in CH$_2$Cl$_2$ (10 mL) was added methanesulfonyl chloride (461 mg, 4.03 mmol). After 18 hours, the mixture was washed with 1N HCl and brine, dried (MgSO$_4$), and concentrated to give 865 mg (90%) of product as an off-white solid m.p. 120°–122° C.

$^1$H NMR (DMSO-d$_6$): δ9.36 (s, 1H), 7.15 (dd, J=6.7, 2.2 Hz, 2H), 6.93 (dd, 6.7, 2.2 Hz, 2H), 4.05 (t, J=6.0, 2H), 3.78 (t, J=6.4 Hz, 2H), 2.88 (s, 3H), 2.15 (m, 2H).

Step 4) Preparation of N-[4-(3-Iodo-1-propyloxy)phenyl]methanesulfonamide

A solution of N-[4-(3-chloro-1-propyloxy)phenyl]methanesulfonamide (1.03 g, 3.90 mmol) and sodium iodide (1.75 g, 11.70 mmol) in acetone (15 mL) was heated under reflux for 18 hours. The mixture was concentrated, taken up in EtOAc, and washed with brine, 10% aqueous sodium bisulfite, and brine. The organic phase was dried (MgSO$_4$) and concentrated to give 1.34 g (96%) of product as an off-white solid m.p. 109°–111° C.

$^1$H NMR (DMSO-d$_6$): δ9.36 (s, 1H), 7.15 (dd, J=6.7, 2.2 Hz, 2H), 6.93 (dd, J=6.7, 2.2 Hz, 2H), 3.98 (t, J=6.0 Hz, 2H), 3.38 (t, J=6.9 Hz, 2H), 2.88 (s, 3H), 2.18 (m, 2H).

Step 5) Preparation of N-[4-(3-Methylamino-1-propyloxy)phenyl]methanesulfonamide Hydriodide A mixture of N-[4-(3-iodo-1-propyloxy)phenyl]methanesulfonamide (1.32 g, 3.72 mmol), THF (8 mL), and 40 wt % methylamine in water (16 mL, 0.186 mol) was stirred at room temperature for 2 hours. The mixture was concentrated to give a brown oil, taken up in 2:1 EtOH/toluene, and concentrated to give 1.42 g (99%) of product as a pink solid m.p. 104°–107° C.

$^1$H NMR (DMSO-d$_6$): δ7.15 (dd, J=6.7, 2.2 Hz, 2H), 6.92 (dd, J=6.7, 2.2 Hz, 2H), 4.02 (t, J=6.0 Hz, 2H), 3.06 (t, J=7.5 Hz, 2H), 2.88 (s, 3H), 2.60 (s, 3H), 2.02 (m, 2H).

Step 6) Preparation of N-[4-[3-[Methyl(1-methyl-1H-benzimidazol-2-yl)amino]propoxy]phenyl]methanesulfonamide Hydrochloride A mixture of N-[4(3-methylamino-1-propyloxy)-phenyl]methanesulfonamide hydriodide (1.40 g, 3.62 mmol), 2-chloro-1-methylbenzimidazole (0.90 g, 5.42 mmol), diisopropyl ethylamine (1.40 g, 10.84 mmol), and 3-methyl-1-butanol (55 mL) was heated under reflux for 41 hours and concentrated. Purification by flash chromatography (2% MeOH/CH$_2$Cl$_2$) gave a brown solid. The HCl salt was made with saturated methanolic HCl (15 mL). Recrystallization from EtOH (twice) gave 360 mg (26%) of product as a white solid m.p. 227°–229° C.

$^1$H NMR (DMSO-d$_6$): δ13.65 (br s, 1H), 9.37 (s, 1H), 7.57 (m, 1H), 7.45 (m, 1H), 7.31 (m, 2H), 7.09 (d, J=9.0 Hz, 2H), 6.87 (d, J=9.0 Hz, 2H), 4.03 (t, J=6.0 Hz, 2H), 3.79 (s, 3H), 3.75 (t, J=7.0 Hz, 2H), 3.29 (s, 3H), 2.84 (s, 3H), 2.15 (m, 2H).

IR (KBr, cm$^{-1}$): 1650 (C=N).

MS (m/e): 389 (MH+).

Anal Calcd: C, 53.70; H, 5.93; N, 13.18; Found: C, 53.47; H, 5.91; N, 12.82.

EXAMPLE 11

N-[4[[3-[Methyl(1-methyl-1H-benzimidazol-2-yl)amino]propyl]thio]phenyl]methanesulfonamide Hydrochloride

Step 1) Preparation of 1-Chloro-3-(4-nitrothiophenoxy)propane

To a cooled (10° C.), stirred suspension of KOtBu (8.9 g, 0.080 mol) in DMSO (40 mL) was added a solution of 4-fluoronitrobenzene (11.2 g, 0.080 mol) and 3-chloropropanethiol (8.8 g, 0.080 mol) in DMSO (40 mL) over 10 minutes. The mixture was stirred at room temperature for 3.5 hours, diluted with water (1000 ml), and extracted with ether. The extracts were washed with brine, dried (MgSO$_4$), and concentrated. Purification by flash chromatography (10% EtOAc/hexane) gave 6.2 g (34%) of product as a yellow solid m.p. 45°–48° C.

$^1$H NMR (DMSO-d$_6$): δ8.14 (d, J=9.1 Hz, 2H), 7.53 (d, J=9.1 Hz, 2H), 3.76 (t, J=6.4 Hz, 2H), 3.24 (t, J=7.0 Hz, 2H), 2.08 (m, 2H).

Step 2) Preparation of 1-Chloro-3-(4-aminothiophenoxy)propane

A mixture of 1-chloro-3-(4-nitrothiophenoxy)propane (1.00 g, 4.32 mmmol), stannous chloride dihydrate (4.87 g, 21.58 mmol), and EtOH was heated under reflux for 3 hours. The mixture was cooled, 2.5 N NaOH (21 mL) was added, and the precipitate was removed by filtration. The filtrate concentrated to 10 mL and extracted with EtOAc. The extracts were dried (MgSO$_4$) and concentrated to give 855 mg (98%) of product as a brown oil.

$^1$H NMR (DMSO-d$_6$): δ7.10 (d, J=8.6 Hz, 2H), 6.53 (d, J=8.6 Hz, 2H), 5.24 (s, 2H), 3.69 (t, J=6.4 Hz, 2H), 2.79 (t, J=6.9 Hz, 2H), 1.86 (m, 2H).

Step 3) Preparation of N-[4-(3-Chloro-1-propylthio)phenyl]methanesulfonamide To a cooded (5° C.) solution of 1-chloro-3-(4-aminothiophenoxy)propane (4.9 g, 0.024 mol) and pyridine (2.1 g 0.027 mol) in CH$_2$Cl$_2$ (50 mL) was added methanesulfonyl chloride (3.1 g, 0.027 mol). The mixture was stirred at room temperature for 16 hours, washed with 2 N HCl, brine, dried (MgSO$_4$), and concentrated. Recrystallization from EtOH gave 4.0 g (59%) of product as a pink solid m.p. 61°–63° C.

$^1$H NMR (DMSO-d$_6$): δ9.77 (s, 1H), 7.35 (d, J=8.6 Hz, 2H), 7.17 (d, J=8.6 Hz, 2H), 3.72 (t, J=6.9 Hz, 2H), 3.01 (t, J=6.9 Hz, 2H), 2.98 (s, 3H), 1.95 (m, 2H).

Step 4) Preparation of N-[4-(3-Iodo-1-propylthio)phenyl]methanesulfonamide

A solution of N-[4-(3-chloro-1-propylthio)phenyl]methanesulfonamide (4.0 g, 0.014 mol) and sodium iodide (6.4 g 0.043 mol) in acetone (55 mL) was heated under reflux for 18 hours. The mixture was concentrated, taken up in EtOAc, washed with brine, 10% aqueous sodium bisulfite, brine, dried (MgSO$_4$), and concentrated to give 4.8 g (91%) of product as an off-white and solid m.p. 59°–63° C.

$^1$H NMR (DMOS-d$_6$): δ9.77 (s, 1H), 7.35 (d, J=8.6 Hz, 2H), 7.17 (d, J=8.6 Hz, 2H), 3.33 (t, J=6.9 Hz, 2H), 2.98 (m, 5H), 1.98 (m, 2H).

Step 5) Preparation of N-[4-(3-Methylamino-1-propylthio)phenyl]methanesulfonamide Hydriodide A solution of N-[4-(3-iodo-1-propylthio)phenyl]methanesulfonamide (4.8 g, 0.13 mol), THF (28 mL), and 40 wt % methylamine in water (56 mL) was stirred at room temperature for 2 hours. The mixture was concentrated, taken up in 2:1 EtOH/toluene, and concentrated to give 4.9 g (94%) of product as a brown solid m.p. 80°–83° C.

$^1$H NMR (DMSO-d$_6$): δ7.36 (d, J=8.6 Hz, 2H), 7.18 (d, J=8.6 Hz, 2H), 2.99 (m, 7H), 2.53 (s, 3H), 1.81 (m, 2H).

Step 6) Preparation of N-[4-[[3-[Methyl(1-methyl-1H-benzimidazol-2-yl)amino]propyl]thio]phenyl]methanesulfonamide Hydrochloride A mixture of N-[4-(3-methylamino-1-propylthio)phenyl]methanesulfonamide hydriodide (4.9 g, 0.012 mol), 2-chloro-1-methylbenzimidazole (3.0 g, 0.018 mol), diisopropyl ethylamine (4.6 g, 0.036 mol), and 3-methyl-1-butanol (16 ml) was heated under reflux for 41 hours. The mixture was concentrated and purified by flash chromatography (1% MeOH/CH$_2$Cl$_2$) to give an oil. The HCl salt was made with saturated methanolic HCl (60 mL). The resulting solution was concentrated to give a foam which was stirred in hot EtOH (50 mL) to give 3.96 g (74%) of product as an off-white solid m.p. 208°–210° C. 1 g was recrystallized from EtOH/water to give 875 mg of product m.p. 210°–212° C.

$^1$H NMR (DMSO-d$_6$): δ13.65 (br s, 1H), 9.78 (s, 1H), 7.60 (m, 1H), 7.48(m, 1H), 7.34 (m, 4H), 7.15 (d, J=8.7 Hz, 2H), 3.78 (s, 3H), 3.68 (t, J=7.3 Hz, 2H), 3.25 (s, 3H), 3.02 (t, J=6.8 Hz, 2H), 2.96 (s, 3H), 1.96 (m, 2H).

IR (KBr, cm$^{-1}$): 1650 (C=N).

MS (m/e): 405 (MH+).

Anal Calcd: C, 51.75; H, 5.71; N, 12.70; Found: C, 51.68; H, 5.65; N, 12.43.

We claim:

1. The compounds of formula (I):

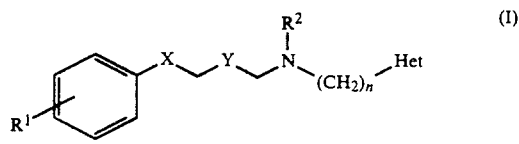

wherein R$^1$ is alkylsulfonamido of 1 to 6 carbon atoms, arylsulfonamido of 6 to 10 carbon atoms, perfluoroalkylsulfonamido of 1 to 6 carbon atoms, prefluoroalkylamido of 1 to 6 carbon atoms, alkylsulfone and alkylsulfoxide of 1 to 6 carbon atoms, NO$_2$, CN, or 1-imidazoyl; R$^2$ is straight or branched alkyl chain of 1 to 6 carbon atoms; X is O, S, or NR$^3$ wherein R$^3$ is H or a straight or branched alkyl chain of 1 to 6 carbon atoms; Y is CH$_2$ or CHOH; n is 0 or 1; Het is

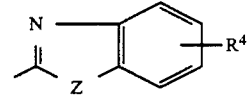

wherein R$^4$ is H, —NHSO$_2$(C$_1$ to C$_6$ alkyl), —NHCO (C$_1$ to C$_6$alkyl) or NO$_2$; and Z is NR$^5$ wherein R$^5$ is H, C$_1$ to C$_6$ alkyl or alkylsulfonamido of 1 to 6 carbon atoms and the pharmaceutically acceptable salts thereof.

2. The compounds of formula (II)

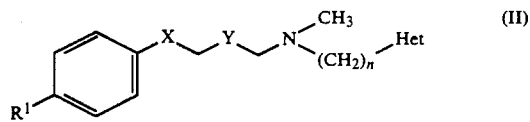

wherein R$^1$ is NO$_2$ or methylsulfonamido; X is O or S; Y is CH$_2$ or CHOH; n is 0 or 1; and Het is

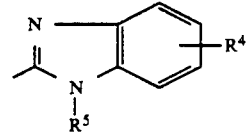

wherein R$^4$ is H or methylsulfonamido; R$^5$ is H or C$_1$ to C$_6$ alkyl and the pharmaceutically acceptable salts thereof.

3. The compound 1-[(1H-benzimidazol-2-yl-methyl)-methylamino]-3-(4-nitrophenoxy)-2-propanol and the pharmaceutically acceptable salts thereof.

4. The compound N-[4-[3-[(1H-benzimidazol-2-yl-methyl)methylamino]-2-hydroxypropoxy]phenyl]methanesulfonamide and the pharmaceutically acceptable salts thereof.

5. The compounds N-[4-[3-[methyl(1-methyl-1H-benzimidazol-2-yl)amino]propoxy]phenyl]methanesulfonamide and the pharmaceutically acceptable salts thereof.

6. The compound N-[4-[[3-[methyl(1-methyl-1H-benzimidazol2-yl)amino]propyl]thio]pheny]methanesulfonamide and the pharmaceutically acceptable salts thereof.

7. A pharmaceutical composition having antiarrhythmic properties which comprises an effective amount of a compound of the formula (I) of claim 1 or its physiologically tolerated acid addition salt and a pharmaceutically acceptable carrier and/or diluent.

* * * * *